United States Patent
Brune et al.

(10) Patent No.: US 6,746,849 B1
(45) Date of Patent: Jun. 8, 2004

(54) ASSAY FOR NUCLEOSIDE DIPHOSPHATE USING A MODIFIED NUCLEOSIDE DIPHOSPHATE KINASE COMPRISING A FLUORESCENT LABEL

(75) Inventors: Martin Hermann Klemens Brune, London (GB); John Edgar Thomas Corrie, London (GB); Martin Ronald Webb, London (GB)

(73) Assignee: Medical Research Council, London (GB)

( * ) Notice: Subject to any disclaimer, the term of this patent is extended or adjusted under 35 U.S.C. 154(b) by 0 days.

(21) Appl. No.: 09/937,296

(22) PCT Filed: May 5, 2000

(86) PCT No.: PCT/GB00/01740

§ 371 (c)(1),
(2), (4) Date: Nov. 14, 2001

(87) PCT Pub. No.: WO00/68418

PCT Pub. Date: Nov. 16, 2000

(30) Foreign Application Priority Data

May 10, 1999 (GB) ............................................. 9910811

(51) Int. Cl.$^7$ .............................. C12Q 1/48; C12N 9/12; G01N 33/53

(52) U.S. Cl. .......................... 435/15; 435/194; 435/7.6; 435/7.9

(58) Field of Search ........................... 435/15, 194, 7.6, 435/7.9

(56) References Cited

U.S. PATENT DOCUMENTS

| | | | |
|---|---|---|---|
| 4,806,415 A | 2/1989 | Piero | 435/14 |
| 4,923,796 A | 5/1990 | Ulfert et al. | 435/15 |
| 5,741,635 A | 4/1998 | Abhijit et al. | 435/4 |

FOREIGN PATENT DOCUMENTS

| | | |
|---|---|---|
| FR | 2 660 933 | 10/1991 |
| WO | 00 52467 | 9/2000 |

OTHER PUBLICATIONS

Witkowski et al. (1999) 38:11643–11650.*
Abstract of Biondi et al. (1996) FEBS Lett 399:183–187.*
Schneider et al. (1998) J Biol Chem 273:11491–11497.*
Deville–Bonne et al. (1996) Biochemistry 35:14643–14650.*
Izumiya et al. (1995) J Biol Chem 27859–27864.*
A. Miyawaki et al., "Fluorescent Indicators for Ca$^{2+}$ Based on Green Fluorescent Proteins and Calmodulin", Letters to Nature, vol. 388, pp. 882–887, Aug. 28, 1997.
A. Honda et al. "Spatiotemporal Dynamics of Guanosine 3',5'–cyclic Monphosphate Revealed by a Genetically Encoded, Fluorescent Indicator", Proc. Natl. Acad. Sci., vol. 98, No. 5, pp. 2437–2442, Feb. 27, 2001.
S. Karamohamed et al., "Bioluminometric Method for Real–Time Detection of ATPase Activity", Biotechniques, vol. 31, pp. 420–425, 2001.
Gary V. Richieri et al., "Interactions of Long–Chain Fatty Acids and Albumin: Determination of Free Fatty Acid Levels Using the Fluorescent Probe ADIFAB", Biochemistry, vol. 32, pp. 7574–7580, 1993.
R. Takashi et al., "A Fluorimetric Method for Continuously Assaying ATPase: Application to Small Specimens of Glycerol–Extracted Muscle Fibers", Analyical Biochemistry, vol. 92, pp. 375–382, 1979.
B. L. Strehler, "Adenosine–5'–triphosphate and Creatin e Phosphate Determination with Luciferase", Methods of Enzymatic Analysis. 2$^{nd}$ ed. New York: Academic Press, pp. 2112–2126.
W. Lamprecht et al., "Determination with Hexokinase and Glucose–6–phosphate Dehydrogenase", Methods of Enzymatic Analysis. 2$^{nd}$ ed. New York: Academic Press, pp. 2101–2110.
V. Schauer–Vukasinovic et al., "Rational Design of a Calcium Sensing System Based on Induced Conformational Changes of Calmodulin", J. Am. Chem. Soc., vol. 119, pp. 11102–11103, 1997.
D. Jaworek et al., "Adenosine–5'–diphosphate and Adenosine–5'–monphosphate", Methods of Enzymatic Analysis, 2$^{nd}$ ed. New York: Academic Press, pp. 2127–2131.
Simon–Peter Williams et al., "Estimation of the Intracellular Free ADP Concentration by $^{19}$F NMR Studies of Fluorine–Labeled Yeast Phosphoglycerate Kinase in Vivo", Biochemistry, vol. 32, pp. 4895–4902, 1993.
Li Qing Zhou et al., "Periplasmic Binding Protein Based Biosensors 1. Preliminary Study of Maltose Binding Protein as Sensing Element for Maltose Biosensor", Biosensors & Bioelectronics, vol. 6, pp. 445–450, 1991.
J. S. Marvin et al., "Engineering Biosensors by Introducing Fluorescent Allosteric Signal Transducers: Construction of a Novel Glucose Sensor", J. Am. Chem. Soc., vol. 120, pp. 7–11, 1998.
M. Brune et al., "Direct, Real–Time Measurement of Rapid Inorganic Phosphate Release Using a Novel Fluorescent Probe and Its Application to Actomyosin Subfragment 1", Biochemistry, vol. 33, No. 27, pp. 8262–8271, 1994.

\* cited by examiner

*Primary Examiner*—Rebecca E. Prouty
*Assistant Examiner*—David Steadman
(74) *Attorney, Agent, or Firm*—Wenderoth, Lind & Ponack, L.L.P.

(57) ABSTRACT

Nucleoside diphosphates (NDPs) are detected or measured by following the dephosphorylation of the phosphoenzyme form of nucleoside diphosphate kinase (NDPK), and nucleoside triphosphates (NTPs) are detected or measured by following the phosphorylation of NDPK to its phosphoenzyme form. A typical process involves (a) causing NDP in sample to bind to NDPK phosphoenzyme, or causing NTP in sample to phosphorylate NDPK and (b) detecting a change in a characteristic of the enzyme which differs between its phosphorylated and unphosphorylated forms. This may be aided by labelling the enzyme. Quantitative data can be obtained. Both in vivo and in vitro measurements can be made.

3 Claims, 7 Drawing Sheets

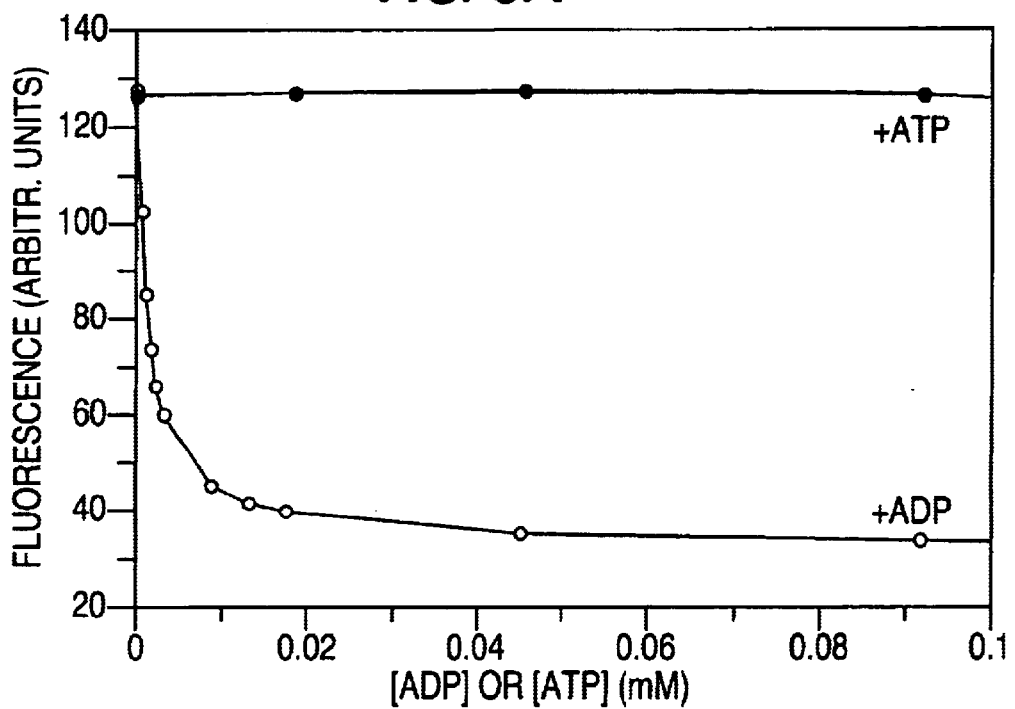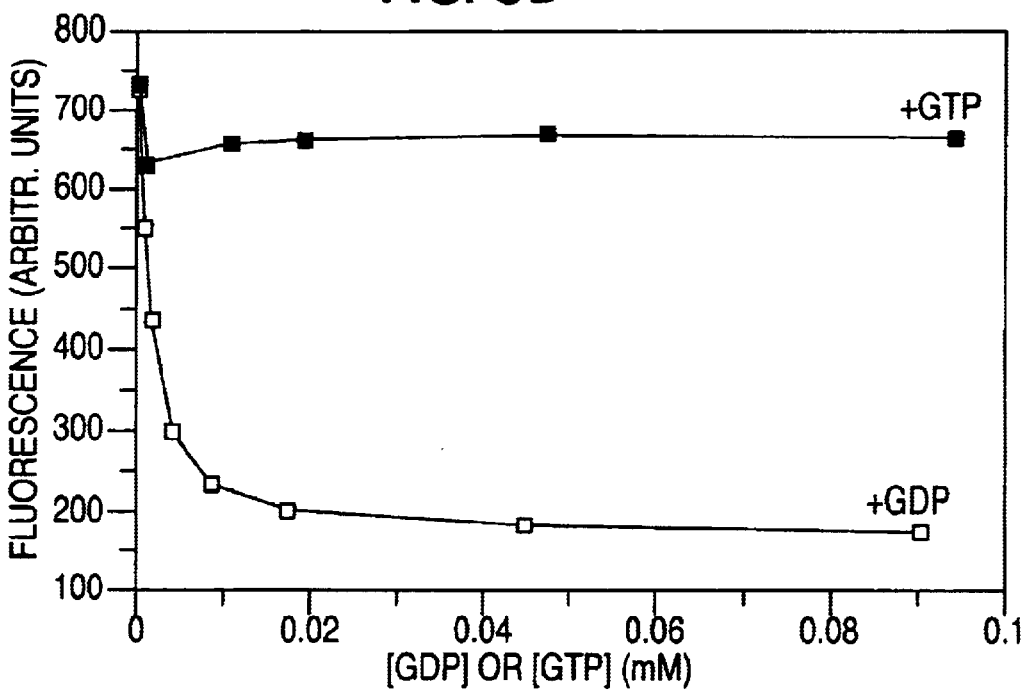

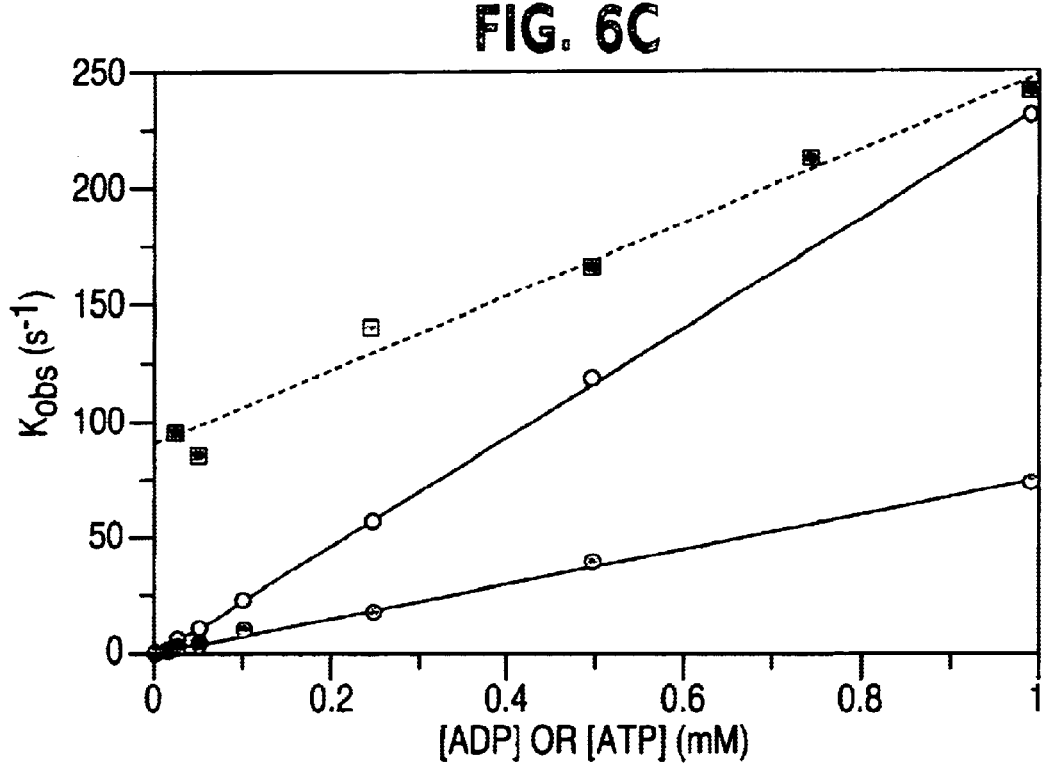

SEQUENCE LISTING

<160> NUMBER OF SEQ ID NOS: 2

<210> SEQ ID NO 1
<211> LENGTH: 145
<212> TYPE: PRT
<213> ORGANISM: Myxococcus xanthus

<400> SEQUENCE: 1

```
Met Ala Ile Glu Arg Thr Leu Ser Ile Ile Lys Pro Asp Gly Leu Glu
 1               5                  10                  15

Lys Gly Val Ile Gly Lys Ile Ile Ser Arg Phe Glu Glu Lys Gly Leu
            20                  25                  30

Lys Pro Val Ala Ile Arg Leu Gln His Leu Ser Gln Ala Gln Ala Glu
        35                  40                  45

Gly Phe Tyr Ala Val His Lys Ala Arg Pro Phe Lys Asp Leu Val
    50                  55                  60

Gln Phe Met Ile Ser Gly Pro Val Val Leu Met Val Leu Glu Gly Glu
 65                  70                  75                  80

Asn Ala Val Leu Ala Asn Arg Asp Ile Met Gly Ala Thr Asn Pro Ala
                85                  90                  95

Gln Ala Ala Glu Gly Thr Ile Arg Lys Asp Phe Ala Thr Ser Ile Asp
            100                 105                 110

Lys Asn Thr Val His Gly Ser Asp Ser Leu Glu Asn Ala Lys Ile Glu
            115                 120                 125

Ile Ala Tyr Phe Phe Arg Glu Thr Glu Ile His Ser Tyr Pro Tyr Gln
        130                 135                 140

Lys
145
```

<210> SEQ ID NO 2
<211> LENGTH: 145
<212> TYPE: PRT
<213> ORGANISM: Myxococcus xanthus
<220> FEATURE:
<221> NAME/KEY: mutagen
<222> LOCATION: 112
<223> OTHER INFORMATION: native Asp replaced with Cys

<400> SEQUENCE: 2

```
Met Ala Ile Glu Arg Thr Leu Ser Ile Ile Lys Pro Asp Gly Leu Glu
 1               5                  10                  15

Lys Gly Val Ile Gly Lys Ile Ile Ser Arg Phe Glu Glu Lys Gly Leu
            20                  25                  30

Lys Pro Val Ala Ile Arg Leu Gln His Leu Ser Gln Ala Gln Ala Glu
        35                  40                  45

Gly Phe Tyr Ala Val His Lys Ala Arg Pro Phe Lys Asp Leu Val
    50                  55                  60

Gln Phe Met Ile Ser Gly Pro Val Val Leu Met Val Leu Glu Gly Glu
 65                  70                  75                  80

Asn Ala Val Leu Ala Asn Arg Asp Ile Met Gly Ala Thr Asn Pro Ala
                85                  90                  95

Gln Ala Ala Glu Gly Thr Ile Arg Lys Asp Phe Ala Thr Ser Ile Cys
            100                 105                 110

Lys Asn Thr Val His Gly Ser Asp Ser Leu Glu Asn Ala Lys Ile Glu
            115                 120                 125
```

```
-continued

Ile Ala Tyr Phe Phe Arg Glu Thr Glu Ile His Ser Tyr Pro Tyr Gln
    130                 135                 140
Lys
145
```

ASSAY FOR NUCLEOSIDE DIPHOSPHATE USING A MODIFIED NUCLEOSIDE DIPHOSPHATE KINASE COMPRISING A FLUORESCENT LABEL

FIELD OF THE INVENTION

The invention relates to assays for nucleoside diphosphates, particularly ADP and GDP, and assays for nucleoside triphosphates, particularly ATP and GTP.

BACKGROUND ART

Nucleoside diphosphates and triphosphates play important roles in biology. ADP is the immediate precursor for the formation of ATP, the universal currency of cellular energy. GDP is a substrate for succinyl CoA synthetase, a key enzyme of the Krebs cycle, and is formed during gluconeogenesis by phosphoenolpyruvate carboxykinase. It is also essential in G-protein signalling, microtubule growth, and visual excitation. UDP is involved in the epimerisation of galactose to glucose, the formation of sucrose, and in the growth of glycogen. CDP is an important group in the synthesis of phosphoglycerides. Nucleoside diphosphates are also the products of reactions catalysed by several major classes of enzymes, such as triphosphatases and kinases, and are therefore produced by many cellular processes, including motility, muscle contraction, DNA synthesis, transcription, translation and nitrogen fixation.

The detection and measurement of nucleoside diphosphates and triphosphates is thus important in the study of biology and metabolism, particularly in bioenergetics.

Assays for ADP and ATP in biological samples based on luciferase have been known for over 20 years [e.g. refs 1, 2, 3, 4]. Bioluminescent assays for ADP and ATP have been described for use in muscle and adipose tissue biopsies [5] and a three-enzyme bioluminescent system utilising luciferase has been reported for use in bacterial cell extracts [6]. A bioluminescent ADP assay optimised for use at high ATP:ADP ratios has been reported [7], but this requires the enzymatic removal of ATP. In general, it is easier to measure ATP in the presence of ADP than to measure ADP in the presence of ATP.

Enzymatic spectrophotometric assays have also been described [e.g. 8].

Assays for GDP and GTP in biological samples are also well known [e.g., refs 9 & 10].

Reference 11 discloses column-based chromatographic assays for GDP, CDP and UDP. Radioactive assays for GDP and GTP have also been described [12, 13]. NMR-based assays for measuring in vivo ADP levels are known for yeast [14], and NMR has also been used to measure ADP and ATP and erythrocytes [15].

DISCLOSURE OF THE INVENTION

According to the present invention, nucleoside diphosphates are detected or measured by following the dephosphorylation of the phosphoenzyme form of nucleoside diphosphate kinase (NDPK), and nucleoside triphosphates are detected or measured by following the phosphorylation of NDPK to its phosphoenzyme form.

The invention thus provides (a) a process for detecting the presence of a nucleoside diphosphate in a sample, comprising the step of detecting the dephosphorylation of the phosphoenzyme form of a nucleoside diphosphate kinase, and (b) a process for detecting the presence of a nucleoside triphosphate in a sample, comprising the step of detecting the phosphorylation a nucleoside diphosphate kinase to the phosphoenzyme form.

The process will typically comprise the steps of:
causing nucleoside diphosphate in sample to bind to NDPK phosphoenzyme, or causing nucleoside triphosphate in sample to phosphorylate NDPK; and
detecting a change in a characteristic of the enzyme which differs between its phosphorylated and unphosphorylated forms.

The term "NDPK" means an enzyme having the activity of the enzyme as EC 2.7.4.6, namely the transfer of the γ-phosphate group of a nucleoside triphosphate ($N_1TP$) to a nucleoside diphosphate ($N_2DP$) via a pin-pong mechanism:

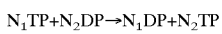

$$N_1TP+N_2DP \rightarrow N_1DP+N_2TP$$

Based on this reaction scheme, the systematic name of NDPK is "ATP:nucleoside-diphosphate phosphotransferase", but the common name is "nucleoside diphosphate kinase". The enzyme has also been variously described as kinase (phosphorylating), nucleoside diphosphate; nucleoside 5'-diphosphate kinase: nucleoside diphosphate (UDP) kinase: nucleoside diphosphokinase: nucleotide phosphate kinase: NM23.

NDPKs have been described for a number of organisms, both prokaryotic and eukaryotic e.g. human, cows, monkeys, mice. Xenopus, oats, peas, potatoes, yeast, *Bacillus subtilis, E. coli, Myxococcus xanthus*, avian myeloblastosis virus etc. These differ by cellular location, molecular weight, oligomeric structure, isoelectric point, reaction kinetics, substrate preference, pH optimum, pH range, temperature optimum, cation requirements ($Mn^{2+}$, $Mg^{2+}$, $Co^{2+}$, $Ca^2$ etc.), and various isoforms have been described. Given the variety of suitable enzymes available, the skilled person can easily select and purify a NDPK to suit any particular situation.

The NDPK enzyme uses a ping-pong mechanism, transferring the γ-phosphate from a nucleoside triphosphate ($N_1TP$) to an active site histidine to form a phosphoenzyme intermediate, and then to a nucleoside diphosphate ($N_2DP$). The invention is based on the finding that the phosphoenzyme intermediate is stable over a time-scale that allows its detection and measurement. Other enzymes that phosphorylate nucleoside diphosphates via a phosphoenzyme intermediate, preferably with a single binding site for nucleotide, may also be used in the invention.

The phosphoenzyme is able to transfer its phosphate group to $N_2DP$ in a sample to form the corresponding $N_2TP$. Detection of this transfer can therefore be used for the detection of nucleoside diphosphate. To detect nucleoside diphosphate according to the invention, therefore, phosphoenzyme is required as a reagent. This can be readily formed by, for example, incubating NDPK with excess NTP, typically ATP. Formation of phosphoenzyme in this way is facilitated by removing $Mg^{2+}$ [16], for instance by using EDTA. Chemical phosphorylation of histidine using phosphormamide as a phosphorylating agent may also be used [17].

The phosphoenzyme can be isolated for use as a reagent. It has been found that the phosphoenzyme can be stored on ice for over 48 hours without dephosphorylation, and can be stored for longer periods (at least 5 months) at −80° C. (although repeated freeze-thawing results in some dephosphorylation). The stability of the phosphoenzyme over the time range needed for its preparation, and subsequently for monitoring kinetic events such as the release of ADP from an ATPase, is particularly advantageous.

When added to a sample containing NDP, the phosphoenzyme is dephosphorylated by the transfer of its phosphate group to the NDP. When added to a sample containing NTP, the phosphoenzyme is formed by the transfer of the NTP γ-phosphate group to the enzyme. The invention relies on the ability to distinguish between the phosphorylated and dephosphorylated forms of NDPK.

In order to distinguish the phosphorylated and unphosphorylated forms of NDPK, any suitable measurable change can be used.

For instance, intrinsic properties of the enzyme can be used. Depending on the particular NDPK chosen, the following methods are examples of how dephosphorylation/phosphorylation may be detected, with varying levels of sensitivity:

The location of a phosphate (i.e. either bound to NDPK, or as the γ-phosphate of a NTP) can be ascertained by following the $^{31}P$ NMR spectrum.

Protons whose environment changes upon dephosphorylation can be detected by, for instance NMR.

Dephosphorylation may cause a change in the fluorescence of a tryptophan residue in the protein [e.g., ref 18].

Dephosphorylation can be detected by following the loss of $^{32}P$ from radio-labelled phosphoenzyme. The radioisotope can be conveniently incorporated into NDPK by using [γ-$^{32}P$]ATP.

Circular dichroism, or any other suitable spectrometric technique, can detect conformational changes which occur on dephosphorylation.

Dephosphorylation may result in a change in surface plasmon resonance properties.

Rather than using properties inherent in the wild-type enzyme, it may be desired to modify the enzyme in some way. This may also be important where dephosphorylation of the NDPK of choice does not exhibit an intrinsic measurable change which can be readily followed.

One particularly preferred modification is the addition of a fluorescent label to the enzyme, typically via a cysteine residue. If the wild-type protein lacks a suitable cysteine residue e.g. the NDPK of *Myxococcus xanthus* (SEQ ID NO: 1), this can easily be introduced by mutagenesis [e.g. 19]. A suitable position for mutation can easily be determined by the skilled person, whilst ensuring that the mutation does not disrupt the enzymatic activity [e.g. 20]. At any given amino acid residue, particular labels may give better results than others. Suitable combinations of label and residue can be determined by routine experimentation.

Preferred fluorescent labels are based around coumarin. Particularly preferred is N-[2-(iodoacetamido)ethyl]-7-diethylaminocoumarin-3-carboxamide [21: FIG. 1], referred to simply as 'IDCC' hereafter. This is preferably attached to a cysteine residue, and preferably exhibits a high fluorescence when NDPK is phosphorylated, and a low fluorescence when NDPK is dephosphorylated. When suitably attached to NDPK, this label offers the advantage that the phosphoenzyme can detect small quantities of ADP in the presence of much higher concentrations of ATP. This is extremely important for experiments in situations where ATP levels are high e.g. in single muscle fibres. It is also able to respond very quickly to changes in ADP levels, and gives a large signal change over a range of several hundred micromolar.

Other labels which can be introduced in similar ways include ESR labels, luminescent labels, phosphorescent labels, and other suitable chromophores.

It will be appreciated that some of the various options available to the skilled person are more suitable than others for detecting the phosphorylation/dephosphorylation of the enzyme in real-time. Fluorescence is highly suitable for real-time detection, whereas methods such as those using radio-labels are more suitable for measuring end-points.

The nucleoside diphosphate/triphosphate which is assayed must be a substrate of the NDPK being utilized. Various NDP substrates have been described [e.g. 22, 23, 24] including ADP, CDP, GDP, UDP, IDP, XDP, their deoxy-derivatives (e.g. dADP, dCDP, dGDP, dTDP, dUDP). 6-aza-UDP, 8-bromo-IDP, 8-aza-GDP, and 8-aza-UDP, and adenosine 5'-methylene diphosphate. Each of these compounds is phosphorylated by the phosphoenzyme (with varying reaction affinities and kinetics, depending on both the NDPK and the substrate being utilised), and can thus be assayed according to the invention.

The invention is preferably used to detect and measure ADP or GDP. Accordingly, a NDPK may be chosen which shows a preference towards one of these substrates.

In preferred embodiments of the invention, the detection process gives quantitative data, that is to say the invention provides a process for quantifying nucleoside diphosphate or triphosphate in a sample. This will typically involve the step of relating a change in the detectable characteristics of a NDPK to a concentration of NDP or NTP. It will be appreciated that this may require a calibration to be performed (e.g. for measuring dephosphorylation via a fluorescent label such as IDCC) or comparison with a standard. Calibration will typically be performed for the desired range of concentrations to be measured.

In a first quantitative aspect, the amount of nucleoside diphosphate or nucleoside triphosphate is determined by measuring the decrease (NDP) or increase (NTP) in the level of phosphoenzyme after the addition of phosphoenzyme (NDP) or unphosphorylated enzyme (NTP) to a sample.

In a second quantitative aspect, the rate of production of nucleoside diphosphate or triphosphate can be determined by following the decrease (NDP) or increase (NTP) in the level of phosphoenzyme over time. By fitting the measured values to a suitable mathematical model (e.g. a simple model based on first-order exponential decrease), the rate of nucleoside diphosphate or triphosphate production can be determined. In this aspect, dephosphorylation of the phosphoenzyme (NDP) or phosphorylation of the enzyme (NTP) is preferably measured using a real-time detection method.

The process of the invention is preferably suitable for use either in vivo or vitro. The method is preferably suitable for in situ use in a muscle fibre, and is preferably gives data suitable for calculating the rate of ADP release from actomyosin.

As well as the step of detecting the dephosphorylation of the phosphoenzyme (NDP-related aspects), the process will usually comprise the initial step of adding NDPK phosphoenzyme to a sample of interest. This may be preceded by the preparation of phosphoenzyme from unphosphorylated NDPK.

The process may also include a step of analysing any data obtained during the process, such as fitting the data to an equation in order to derive quantitative values.

The process preferably avoids the use of reagents such as theophylline, desdanine and $Ag^+$, which may inhibit the NDPK activity.

As well as the above processes, the invention provides reagents for use in the processes.

The invention provides NDPK which is modified to carry a label which gives a different detectable signal when the enzyme is phosphorylated from when it is unphosphorylated.

The label on the modified NDPK may be a fluorescent group, preferably IDCC.

The label will typically be attached to an amino acid residue in the enzyme. It is preferred to attach the label to a cysteine residue.

A particularly preferred reagent is the NDPK of *M. xanthus* carrying a Asp112→Cys mutation, and carrying an IDCC label at this mutated residue. This reagent as a phosphoenzyme is about three orders of magnitude more sensitive to ADP than to ATP.

The invention also provides a NDPK modified by the attachment of at least one detectable label that is sensitive to the binding of a nucleoside diphosphate.

The invention also provides substrates having these NDPK reagents immobilised thereto. These include columns or beads. This may be used in combination with $^{32}P$-phosphoenzyme, such that ADP in a sample incubated with immobilised NDPK will become radio-labelled in its conversion to ATP. Radioactivity in free solution will therefore indicate the amount of ADP in the original sample.

The invention also provides processes for the production of these NDPK reagents.

Furthermore, the invention provides these NDPK reagents for use as in vivo or in vitro diagnostic reagent.

BRIEF DESCRIPTION OF THE DRAWINGS

FIG. 3 shows a titration of IDCC-labelled phosphoenzyme with ADP/GDP (open symbols ○ and ⋈) and ATP/GTP (closed symbols ● and ▮).

EXAMPLES

Figure 1:
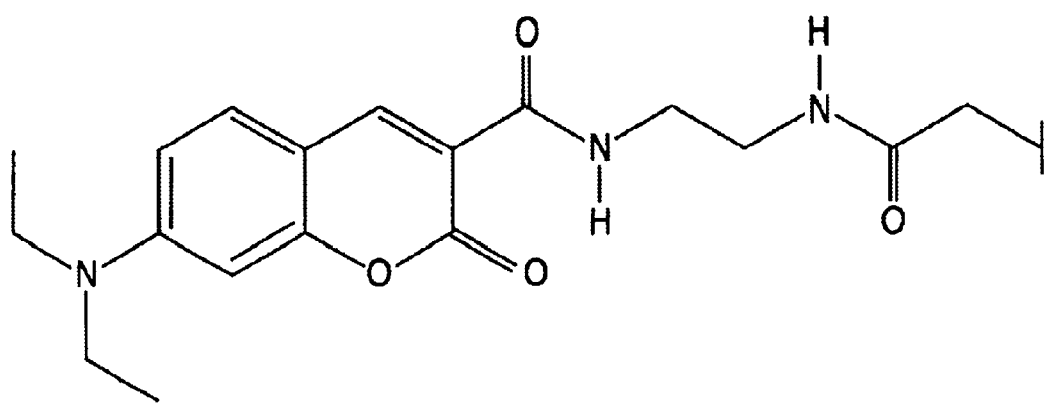
FIG. 1 shows the structure of a preferred fluorescent label, IDCC.

General molecular biology techniques were carried out according to Sambrook et al. [25].

Preparation of NDPK

The NDPK of *M.xanthus* is encoded by the ndk gene, which has been cloned and expressed in *E.coli* [26]. The protein is a homo-tetramer of 16 kDs subunits, it has been characterised, and a crystal structure has been determined [16.27]. The wild-type sequence does not contain any cysteine, so the gene was manipulated to introduce cysteine residues by site-directed mutagenesis in *E. coli* strains TG1 and DH5α using either a phosphothioate-based method [28, produced in kit form by Amersham] or the PCR-based QuickChange kit [Stratagene].

Using the Amersham kit, the 0.8 kg HindIII-EcoRi fragment of pJM5C2A [29] containing the ndk gene from *M.xanthus* was ligated with M13mp19, and the resulting recombinant clones were used to provide single-stranded DNA templates for mutagenesis. For cloning, the mutated ndk genes were cloned back into pJM5C2A. As an alternative, the 0.7 kb BstXI-EcoRl fragment of the M13ndk constructs was ligated into a modified form of the Invitrogen™ pRSetA expression vector, whose coding sequence for a histidine tag fused to the N-terminus of NDPK had been removed. This yielded the 3.5 kb pRSndkX series of plasmids, where the final "X" is a number in a series of ndk mutations.

pRSndk was also used as a template for the QuickChange method.

Various mutant proteins containing cysteine residues were prepared, including D112C (i.e. Asp-112 was mutated to Cys (SEQ ID NO:2)) and D62C. Positions for mutations were typically chosen on the basis of their proximity to the nucleotide-binding cleft seen in the crystal structure [16].

The mutant D112C gene was produced in plasmid pRSndk4, which was also used for expression. For best results, freshly-transformed cells were used for starter cultures, 200 μl calcium-competent BL21 cells [Novagen] were incubated with 2 ng pRSndk4 plasmid DNA for 30 minutes on ice. Half of this mixture was then spread onto an LB agar plate containing 0.1 mg/ml ampicillin and incubated overnight at 37° C. Plates typically contained 50–100 colonies. 100 ml LB medium containing 0.1 mg/ml ampicillin was inoculated with 2–3 colonies from the plate and grown for 9 hours at 37° C. until cells had just entered stationary phase. For the main culture. 8×500 ml LB+ampicillin was inoculated with 10 ml started culture and incubated at 37° C. for 6 hours, after which time the cells had typically reached $OD_{595}$ of 0.38. At this point, 0.5 mg/ml IPTG was added to each flask, and the cells grown for a further 16 hours. Cells were harvested by centrifugation in a Beckman L2 centrifuge at 3800 rpm and 20° C. for 20 minutes. The pellet was resuspended in 100 ml Buffer A (20 mM Tris-HCl.pH 8.2. 1 mM EDTA) and stored at −80° C. Approx. 35 ml of the frozen cell suspension was lysed by slow thawing and then sonication. The supernatent (i.e. crude extract) was retained. Expression levels were determined by SDS-PAGE, $NDPK^{D112C}$ made up >50% cytosolic protein.

NDPK purification involved two column chromatography steps. First, after adjusting pH and ionic strength using Buffer A+10 mM DTT, the crude extract (approx. 200 ml) was loaded onto a 120 ml Q-Sepharose ion-exchange column at 4° C. and a flow rate of 2.0 ml/min. The column was washed with 1 volume buffer and eluted with a continuous linear gradient (500 ml) from 0–0.3M NaCl at 1 ml/min flow rate. The bulk of NDPK (about 80%) does not bind to the resin under these conditions.

After concentration using an Amicon YM10 ultrafiltration membrane, the eluate was loaded onto a G-100 Sepharose gel filtration column in Buffer A. At a flow-rate of 1.0 ml/min, the elution profile showed 2 peaks. The first contained DNA, and the second contained proteins. Fractions containing NDPK were pooled and concentrated as before.

It was confirmed that there was no contamination with *E. coli* NDPK, which has a similar sequence and is also a tetramer [30]. Mass spectrometry data showed that the purified protein was a single species with MW 15993±1 Da, matching the calculated MW of the mutant protein minus the N-terminal Met, which was shown to be missing when expressed in *E.coli* [16]. The yield of pure NDPK$^{D112C}$ from a 4-liter culture was around 300 mg.

Fluorescent Labelling of NDPK

NDPK$^{D112C}$ was incubated with a 2.5-fold excess of IDCC (FIG. 1) in 50 mM Tris/HCl, pH 8.1 for 1 hour at 37° C. In a typical experiment, the volume of the labelling solution was 3 ml and the concentration of NDPK$^{D112C}$ was 150 µM. After incubation, this solution was filtered through a 0.2 µM Acrodisc filter (Gelman) and loaded onto a PD10 desalting column (Pharmacia) equilibrated in Buffer B (10 mM Tris-HCl, pH 8.0. 1 mM EDTA). The eluate (approx. 6 ml) containing labelled protein was immediately loaded onto a 25 ml Q-Sepharose column equilibrated in Buffer B. followed by a 20 ml linear gradient from 0–0.1M NaCl. The labelled protein was completely eluted before the gradient was applied, and was concentrated in the same way as unlabelled protein. The concentration of the protein was determined using absorbance spectroscopy, assuming that the absorbance spectrum of the fluorophore was unaltered ($\epsilon^{430nm}$ 46800 M$^{-1}$ cm$^{-1}$). This concentration value agree with that measured by a colorimetric assay using a bovine serum albumin standard curve. After correcting for the absorbance of IDCC at 276 nm (0.198 of that at 430 nM in the dithiothreitol adduct), the molar extinction coefficient for NDPK could be calculated at $\epsilon^{276nm}$ 7600 M$^{-1}$cm$^{-}$.

The yield after labelling and purification was typically 65%. This high yield indicates that the thiol group of Cys-112 is easily accessible. Mass spectrometry revealed that one molecule IDCC was incorporated per protein molecule, with no indication of second-site labelling, and the mass was that expected for IDCC-NDPK.

To check that mutation and labelling did not affect oligomerisation, the MW of the complex was determined by sedimentation equilibrium centrifugation. The results indicate that IDCC-NDPK is a tetramer of MW 62.7 kDa (4% lower than that calculated for a tetramer from mass spectrometry data).

Where rapid analysis of the fluorescent properties of a new mutant/fluorophore combination was required, labelling was performed on a smaller scale, typically using a NDPK concentration of 100–200 µl and avoiding the ultrafiltration and Q-Sepharose steps.

Other thiol-reactive environmentally-sensitive fluorescent labels which were tested included MDCC (N-[2-(1-maleimidyl)ethyl]-7-diethylaminocoumarin-3-carboxyamide) [21].

Phosphorylation

IDCC-NPDK was incubated with ATP, typically at a 5-fold excess, but ≦1 mM. The incubation was for 30–45 minutes at 37° C. in either in 10 mM Tris/HCl, pH 8.0, 1 mM EDTA, or in 10 mM PIPES, pH 7.0. 1 mM EDTA. The protein was separated using a PD10 column equilibrated in the same buffer. Typically, more than 90% of the eluted protein was phosphoenzyme. The solution was either used immediately or after storage on ice for up to 48 hours. If necessary, the solution was concentrated using a microcentrifuge concentrator.

Fluorescent Properties

The spectroscopic properties of the phosphoenzyme (IDCC-NDPK-P) were compared with the unphosphorylated form of the enzyme. Data was recorded on a Perkin-Eimer LS50B luminescence spectrometer with a xenon lamp and monochromator slit widths set to 2.5 or 5 nm.

Figure 2A:
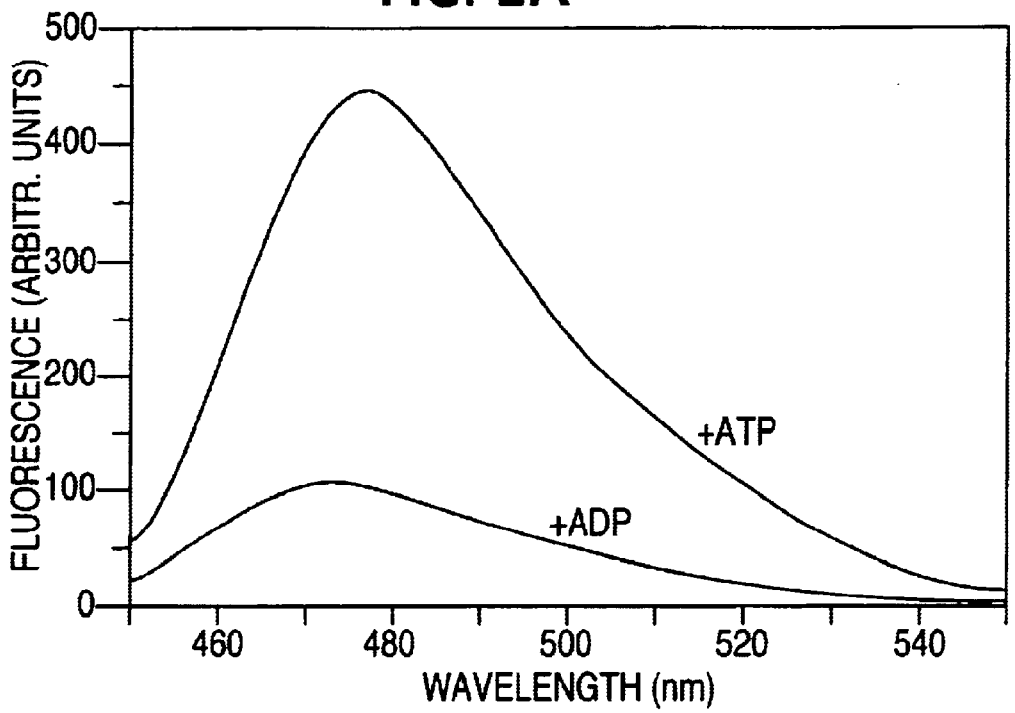
FIG. 2 shows the emission spectra of IDCC-NDPK in the presence of (A) ADP/ATP and (B) GDP/GTP.
Figure 2B:
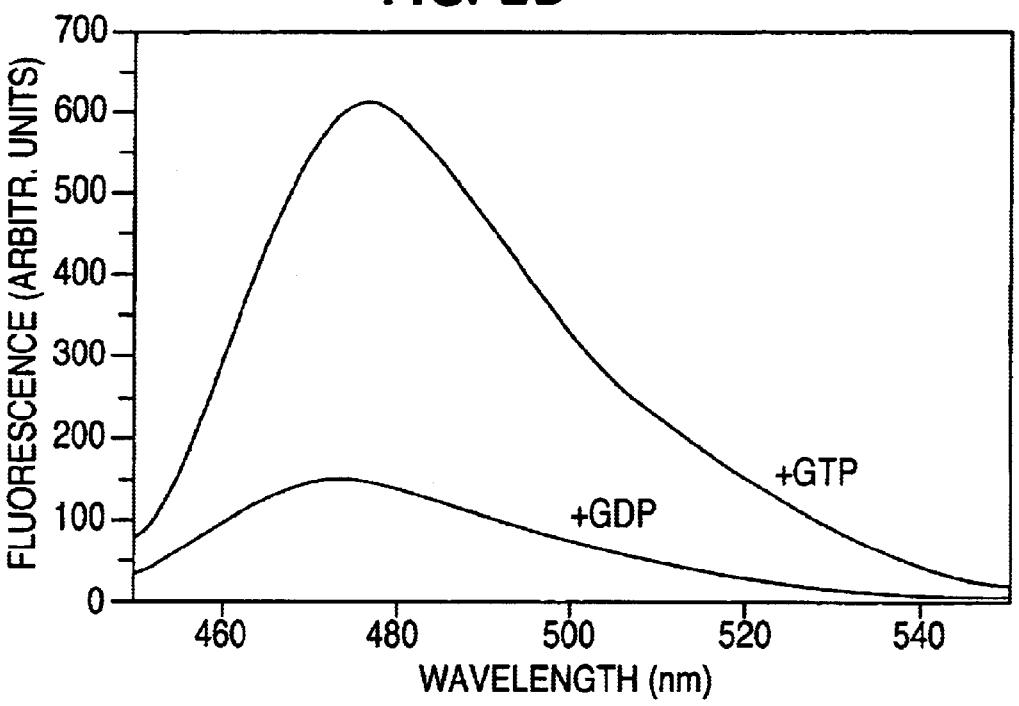

The fluorescence of IDCC-NDPK was 4-fold greater in the presence of 50 µM ATP than in the presence of 50 µM ADP (FIG. 2A). Similar results were obtained with 100 µM GDP/GTP (FIG. 2B). In both cases the spectra were recorded at 20° C. from a 200 µl solution of 2 µM protein in 20 mM PIPES, pH 7.0. 2 mM MgCl$_3$. Excitation was at 441 nm, slit width 5 nm. No correction was made for the small (1%) volume change. These results indicate that IDCC-NDPK~P has a high fluorescence compared with the unphosphorylated form.

A titration of a solution of 2 µM IDCC-NDPK~P with ADP showed a large decrease in the fluorescence signal (FIG. 3A), whereas there was no change with ATP over the same concentration range (<100 µM). Similar data were obtained with GDP/GTP (FIG. 3B). The ADP/ATP assays were carried out at 21° C. in 10 mM Tris/HCl, pH 8.0, 5 mM MgCl$_2$. Excitation was at 432 nm (5 nm slit width) and emission was recorded at 478 nm (2.5 nm slit width). The GDP/GTP assays were carried out at 20° C. in 20 mM PIPES, pH 7.0, 2 mM MgCl$_2$. Excitation was at 441 nm (5 nm slit width) and emission was recorded at 475 nm (5 nm slit width). In both cases data were corrected for the small volume increases. The small decrease at the first addition of GTP in FIG. 3B is due to partial hydrolysis of GTP in the diluted 200 µM stock solution; subsequent GTP additions were from a 2 mM stock solution.

Figure 4A:
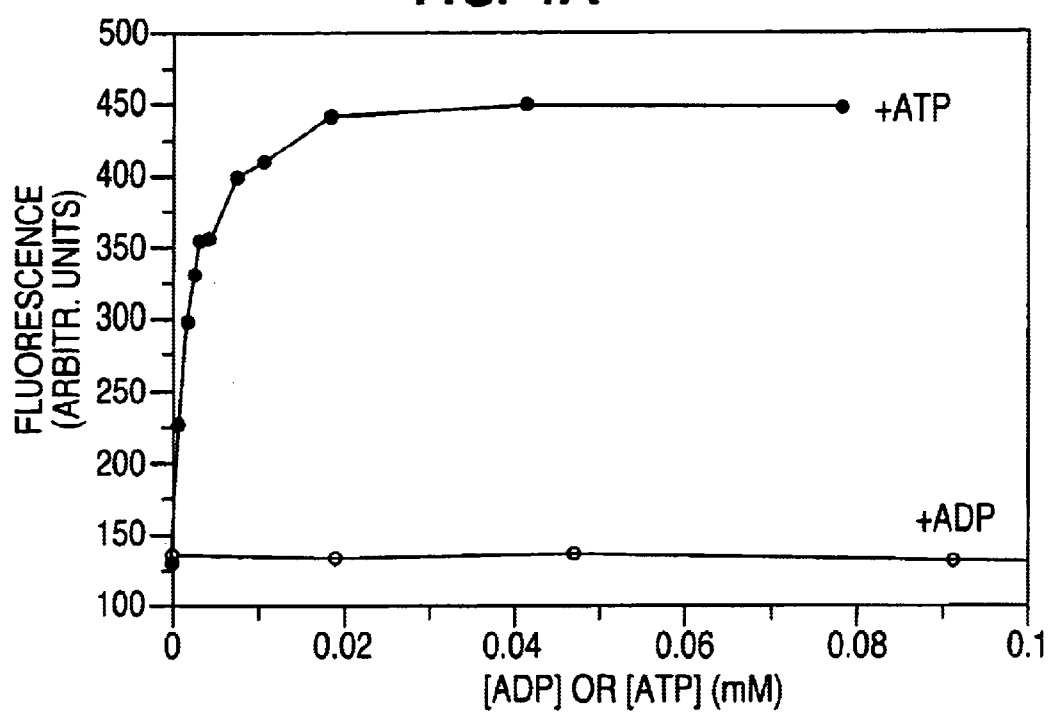
FIG. 4 shows the same experiments using unphosphorylated enzyme.
Figure 4B:
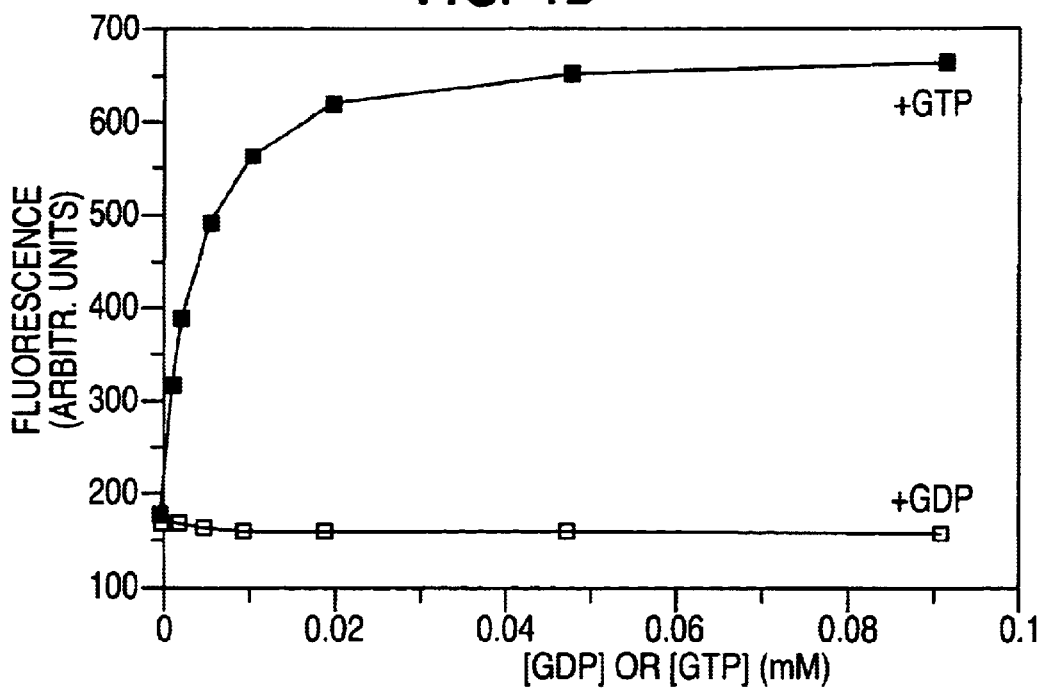

Together with data from unphosphorylated enzyme (FIGS. 4A and 4B), this suggests that most of the fluorescence change is due to phosphorylation/dephosphorylation of the enzyme.

Increasing ADP above 50 µM produces a small fluorescence increase. This is probably due to a non-specific interaction between ADP and NDPK, as suggested for non-labelled wild-type enzyme [18]. The change in fluorescence signal is linear with [ADP] up to at least 50% of the protein concentration.

Figure 5:
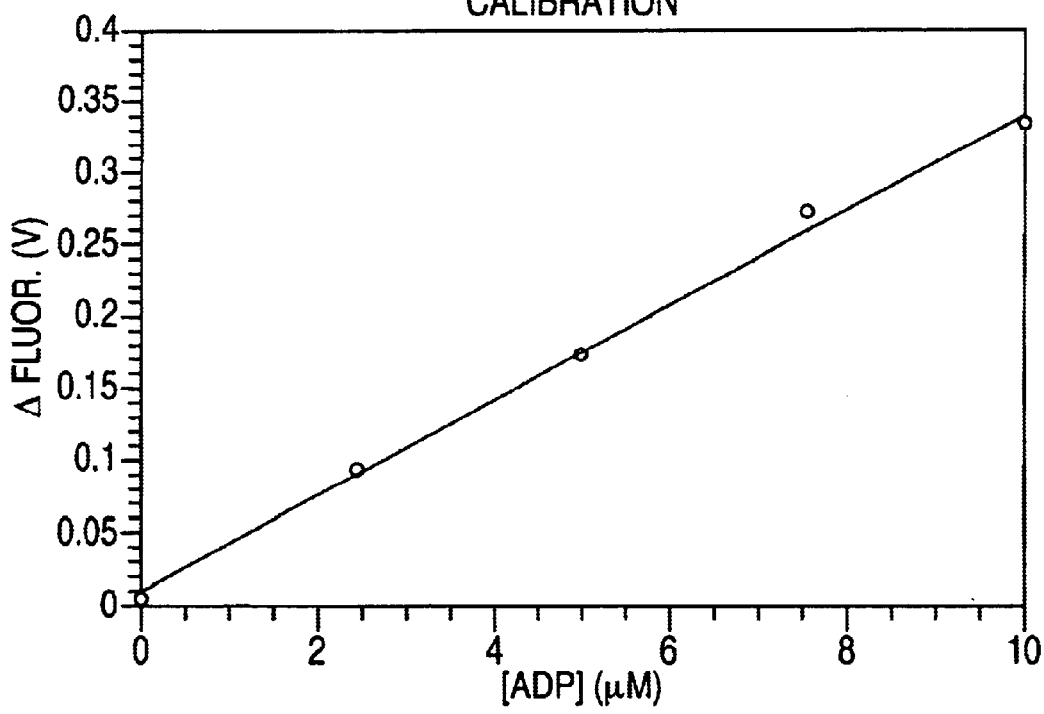
FIG. 5 shows a calibration curve obtained in a stopped flow experiment, indicating how fluorescence change varies with ADP concentration.

To derive quantitative data from the fluorescence measurements, the calibration curve shown in FIG. 5 was plotted. The calibration data were obtained in a stopped flow experiment by mixing 10 µM IDCC-NDPK~P and 50 µM ATP with 0, 2.5, 5.0, 7.5 or 10.0 µM ADP (10 mM PIPES buffer, pH 7.0, 1 mM MgCl$_2$, 20° C.). The amplitudes of the fluorescence change (ΔF) were averaged from two experiments at each concentration and plotted against ADP concentration.

There is a shaft of 6 nm in the absorbance maxima of the fluorophore between IDCC-NDPK and IDCC-NDPK~P, but only 2 nm in the emission maxima. The fluorescence quantum yields for the two forms of the labelled enzyme were determined using as reference the known value of 0.83 for Coumarin 314 in ethanol [31]. There was a 4-fold decrease in the quantum yield when going from phosphorylated (0.22) to unphosphorylated enzyme (0.054), in good agreement with the observed change in emission intensity (FIG. 2), although the quantum yield for the phosphoenzyme was still significantly lower than that for Coumarin 314 in buffer (0.52).

Transient Kinetics

Figure 6A:
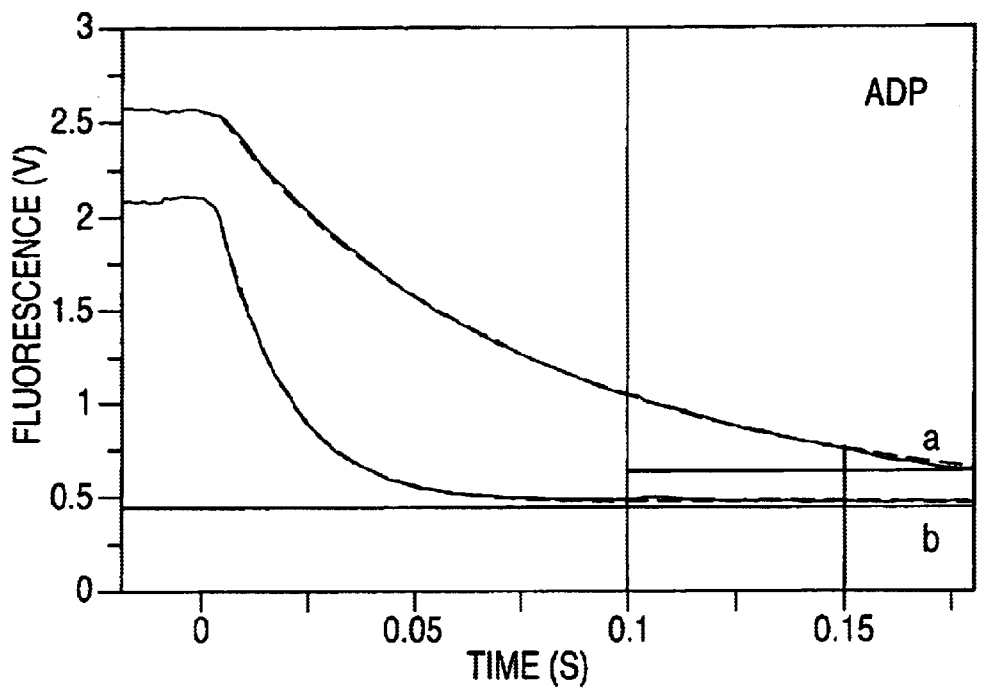
FIG. 6 shows transient kinetic data obtained using stopped-flow fluorescence. The dashed curves represent the best fit to a single exponential equation, 6A & 6B show data obtained with ADP and ATP, respectively, 6C shows a spot of observed rate constants against ADP (○) or ATP (●) concentration. The solid line shows the best fit to a linear equation with the respective deduced second-order rate constants. The dashed line and squares (■) show observed rate constants that were obtained when the ADP titration was repeated in the presence of 1 mM ATP.

Three different transient kinetic measurements were carried out in a stopped-flow apparatus Firstly, the rate of IDCC-NDPK~P dephosphorylation was measured over a range of ADP concentrations. FIG. 6A shows the emission data for mixing 50 µM (a) and 250 µM (b) ADP with 1 µM protein in 20 mM PIPES. pH 7.0, 2 mM MgCl$_2$. The observed rate constants (a: 11.1±0.01 s: b:

$57.2\pm0.07\text{s}^{-1}$) increased linearly in proportion to the increasing ADP concentrations, and a second order rate constant was calculated from the slope of the linear fit, giving $0.21\times10^6$ $\text{M}^{-1}\text{s}^{-1}$ (FIG. 6C).

Figure 6B:
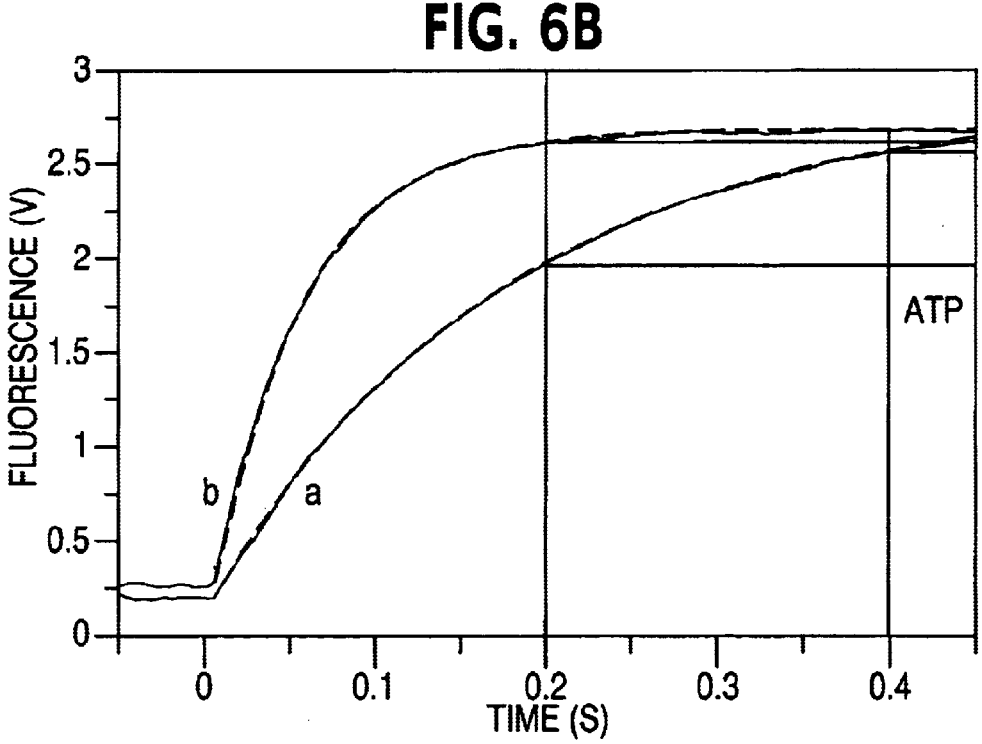

In a second experiment, the rate of phosphoenzyme production was measured by mixing IDCC-NDPK~P enzyme with ATP (FIG. 6B). Again, there was a linear increase in rates with increasing ATP ($5.57\pm0.01$ $\text{s}^{-1}$ at 50 $\mu$M ATP; $18.4\pm0.03$ $\text{s}^{-1}$ at 250 $\mu$M ATP), and the deduced second order rate constant was $0.072\times10^6$ $\text{M}^{-1}\text{s}^{-1}$ (FIG. 6C).

In a third experiment, the rate of dephosphorylation was measured in the presence of varying concentrations of ATP. The observed rates were higher but the intensity changes lower in the presence of ATP than in its absence. From the slope of the dashed line in FIG. 6C (■), the second order rate constant is calculated as $0.135\times10^6$ $\text{M}^{-1}\text{s}^{-1}$ in the presence of ATP. The increase in rate produced by ATP can be explained by considering the enzymatic equilibrium:

ADP+IDCC-NDPK~P≈ATP+IDCC-NDPK

The observed rate is $k_4$[ADP]+$k$.[ATP], and therefore increases with both [ADP] and [ATP].

This rate acceleration is advantageous in muscle fibres, for instance, where ATP levels are usually at least 1 mM. Dephosphorylation of the phosphoenzyme should be very fast, even at ADP concentrations which are initially low.

Measurements in a Single Muscle Fibre

An experiment was performed on a single rabbit psoas muscle fibre in the presence of $Ca^{2-}$, essentially as described in reference 32, with the following modifications. An incubation of the fibre for 10 minutes in rigor solution containing 8U/ml Apyrase to remove background ADP was followed by 10 minutes incubation in loading solution containing 380 $\mu$M IDCC-NDPK~P and 5 nM NPE-caged ATP [the $P^5$-1-(2-nitrophenyl)ethyl ester of ATP]. The fibre was transferred to silicone oil, and ATP (approx. 1 mM) was released by laser flash photolysis (347 nm) at time zero. The temperature during the experiment was 18° C., and the aqueous solutions were pH 7.1 and pCa 4.5. Fluorescence excitation was at 425 nm, and emission was detected through a long-pass filter (450–650 nm).

Figure 7:
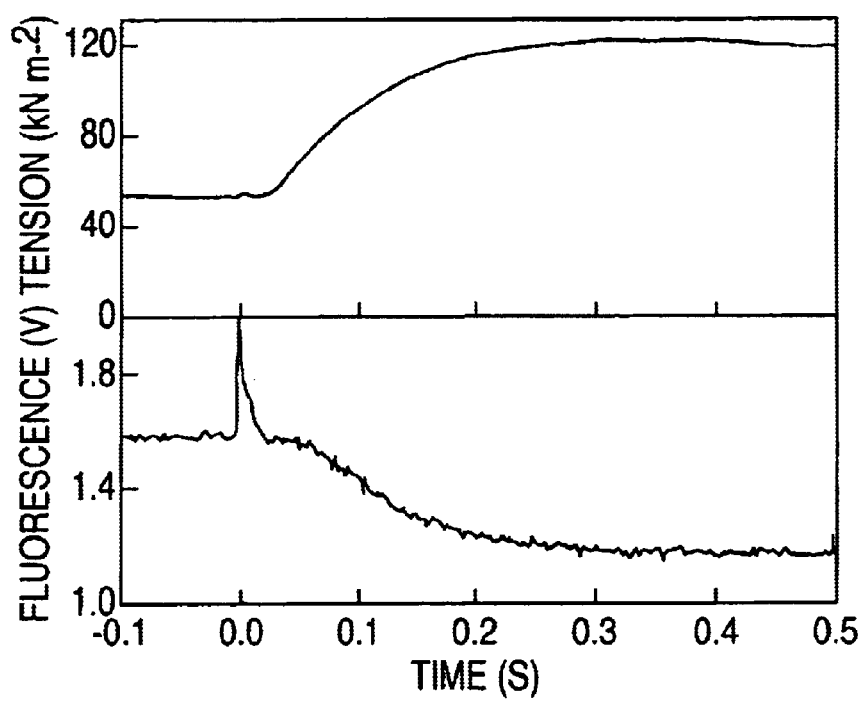
FIG. 7 shows a plot obtained from a single rabbit psoas muscle fibre (skinned), indicating the increase in muscle tension and the accompanying decrease in fluorescence due to dephosphorylation of IDCC-NDPK~P.

The fluorescence trace (bottom curve. FIG. 7) after time zero consists of three parts: first, a flash artefact: then, a lag, during the time for the first ATPase cycle to occur as far as bound ADP: finally, a slow phase of decreasing fluorescence, representing the reaction of IDCC-NDPK~P with ADP. The initial slope of this curve gives the rate of ADP relates from actomyosin as $11\text{s}^{-1}$.

Similar experiments in muscle fibres using NPE-caged ADP to measure ADP production independently from myosin ATPase show that (i) the phosphoenzyme us able to maintain its sensitivity and reactivity for ADP when it is within a muscle fibre (ii) a signal is detectable for ADP released from myosin ATPase (iii) the muscle fibre is developing tension in the expected manner.

Nucleotide Exchange from Human Rho Protein

The rate of nucleotide exchange from a small G protein, rho (which also has GTPase activity), was determined in solution. The rate of hydrolysis was also obtained indirectly.

Human rho protein was prepared in a form containing tightly-bound GDP. In the presence of excess added GTP, nucleotide exchange occurs such that GDP is released into free solution where it can be measured according to the invention. Once GTP is bound to rho, its hydrolysis is slowly catalysed by the protein at a steady-state rate. This creates more GDP, which is measured once it is released.

Figure 8:
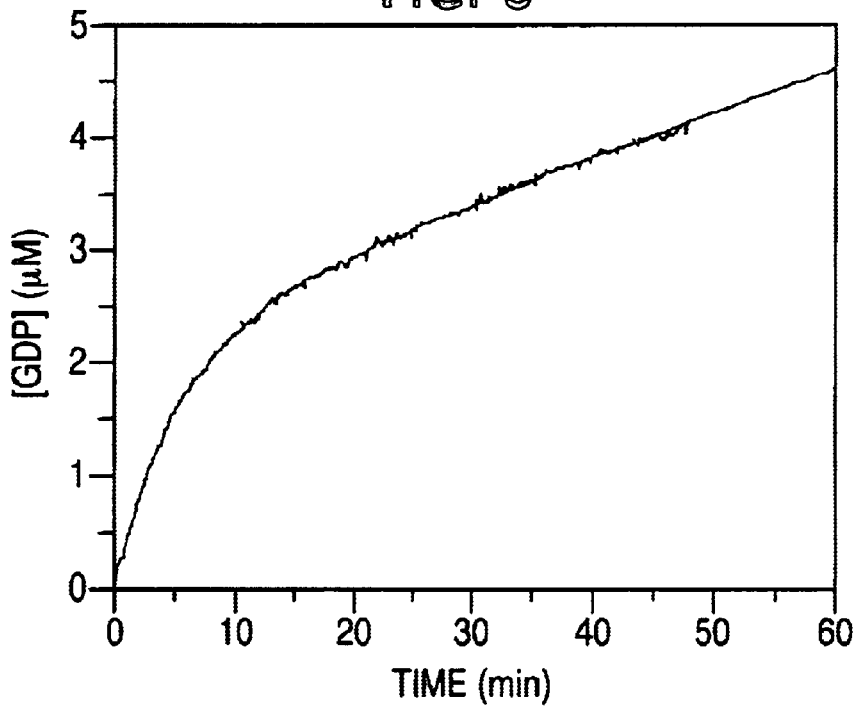
FIG. 8 shows a plot obtained using human rho protein, indicating the release of GDP into solution. Data were fitted to a single-exponential plus linear equation, shown as a solid line.

Fluorescence emission was recorded for a 200 $\mu$l solution containing 20 mM Tris/HCl, pH 7.6, 1 mM $MgCl_2$, 100 mM $(NH_4)_2SO_4$, 10 $\mu$M GTP, and 2 $\mu$M IDCC-NDPK~P. The reaction was started at t=0 by adding 2 $\mu$M Rho.GDP. Excitation was at 440 nm with the emission monochromator set to 475 nm. The temperature was 30° C. The data were normalized using the fluorescence change for 1 $\mu$M GDP obtained from a titration of IDCC-NDPK~P with different GTP/GDP ratios. The data (FIG. 8) were fitted to a single-exponential plus linear equation with a rate constant of 0.196 $\text{min}^{-1}$ for the exponential phase and a slope of 41.2 nM GDP $\text{min}^{-1}$ ($3.43\times10^{-4}$ $\text{s}^{-1}$, after dividing by [Rho]) for the linear phase. The exponential "burst" represents the exchange of GDP bound to rho for GTP. The linear phase represents steady state: exchange of further GTP onto rho is limited by hydrolysis to GDP.

The rates were also measured by 'standard' means, and similar results were found.

It will be understood that the invention is described above by way of example only and modifications may be made whilst remaining within the scope and spirit of the invention.

REFERENCES (the contents of which are incorporated herein in full)

1. Holmsen et al. (1972) *Anal. Biochem.* 46:489–501
2. Kimmich et al. (1975) *Anal Biochem.* 69:187–206
3. Loxdale (1976) *J Physiol (Land)* 240–4P-5P
4. Spielmann et al. (1981) *Anal Biochem* 113:172–178
5. Feradui et al. (1981) *Int J Sports Med* 2:106–109
6. Brovko et al. (1994) *Anal Biochem* 220:410–414
7. Schultz et al. (1993) *Anal Biochem* 215:302–304
8. Tornheim & Schultz (1993) *Anal Biochem* 211:329–330
9. Pogson et al. (1979) *Int J Biochem* 10:995–1000
10. de Azeredo et al. (1979) *Anal Biochem* 95:512–519
11. Sato et al. (1983) *Anal Biochem* 135:431–435
12. Goswami & Pande (1984) *J Biochem Biophys Methods* 9:143–151
13. Cerpovicz & Ochs (1991) *Anal Biochem* 192:197–202
14. Brindle et al. (1990) *Biochem* 29:3295–3302
15. Petersen et al. (1990) *Biochim Biophys Acta* 1035:169–174
16. Williams et al. (1993) *J Mol Biol* 234:1230–1247.
17. Morera et al. (1995) *Biochemistry* 34:11062–11070.
18. Schaertl et al. (1998) *J Biol Chem* 273:5662–5669
19. Sundin et al. (1996) *J. Bacteriol* 178:7120–7128
20. Izumiya & Yamamoto (1995) *J Biol Chem* 270:27859–27864.
21. Corrie (1994) *J Chem Soc. Perkin Trans* 1:2975–2982.
22. Parks & Agarwal in *The Enzymes*, 3rd ed (ed. Boyer), 8:307–333
23. Agarwal et al. (1978) *Methods Enzymol* 51:376–386
24. Jong & Ma (1991) *Arch Biochem Biophys* 291:241–246.
25. Sambrook et al. (1989) *Molecular cloning—a laboratory manual*.
26. Muñoz-Dorado et al. (1990) *J. Biol Chem* 265:2702–2706.
27. Muñoz-Dorado et al. (1990) *J Biol Chem* 265:2707–2712.
28. Olsen et al. (1993) *Meth Enzymol* 217:189–217.
29. Kindly provided by Dr R Williams, Cambridge.
30. Almaula et al (1995) *J Bacteriol* 177:2524–2529.
31. Fletcher & Bliss (1978) *Appl. Phys* 16:289–295.
32. He et al. (1997) *J. Physiol.* 501.1:125–148.

What is claimed is:

1. A process for detecting the presence of a nucleoside diphosphate in a sample, comprising a step of detecting the dephosphorylation of the phosphoenzyme from of a nucleoside diphosphate kinase (NDPK), wherein the NDPK is an NDPK of *Myxococcus xanthus* having the amino acid sequence of SEQ ID NO: 2, which is modified to carry an IDCC label attached to cysteine at position 112 in both the NDPK's phosphorylated and unphosphorylated forms, which label gives a different detectable signal when the enzyme is phosphorylated from which it is unphosphorylated.

2. The process of claim 1, wherein the nucleoside diphosphate is ADP or GDP.

3. The process of claim 1, being a quantitative process.

* * * * *